United States Patent
Nystrom

(10) Patent No.: US 9,511,186 B1
(45) Date of Patent: Dec. 6, 2016

(54) MEDICAL INJECTION SYSTEMS AND PUMPS

(71) Applicant: ACIST Medical Systems, Inc., Eden Prairie, MN (US)

(72) Inventor: Sidney Donald Nystrom, Shoreview, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 652 days.

(21) Appl. No.: 13/800,945

(22) Filed: Mar. 13, 2013

Related U.S. Application Data

(60) Provisional application No. 61/717,434, filed on Oct. 23, 2012.

(51) Int. Cl.
    *A61M 5/142* (2006.01)
    *F04C 18/22* (2006.01)

(52) U.S. Cl.
    CPC .............. *A61M 5/142* (2013.01); *F04C 18/22* (2013.01)

(58) Field of Classification Search
    CPC .............................. A61M 5/142; F04C 18/22
    USPC .......... 418/54, 61.2, 113, 116, 117, 140, 149
    See application file for complete search history.

(56) References Cited

U.S. PATENT DOCUMENTS

| | | |
|---|---|---|
| 553,086 A | 1/1896 | Wheildof |
| 1,101,329 A | 6/1914 | Reattgh |
| 1,238,939 A | 9/1917 | Pfleeger |
| 1,548,981 A | 8/1925 | Clark |
| 1,636,486 A | 7/1927 | Planche |
| 2,517,645 A | 8/1950 | Erikson |
| 3,128,782 A | 4/1964 | Limpert et al. |
| 3,800,760 A * | 4/1974 | Knee .................. F01C 1/22 123/242 |
| 4,207,806 A | 6/1980 | Bimond et al. |
| 4,767,399 A | 8/1988 | Bollish |
| 4,850,980 A | 7/1989 | Lentz et al. |
| 5,312,233 A | 5/1994 | Tanny et al. |

(Continued)

FOREIGN PATENT DOCUMENTS

| | | |
|---|---|---|
| CH | 146646 A | 4/1931 |
| DE | 4322560 A1 | 1/1994 |

(Continued)

OTHER PUBLICATIONS

Wu Yujuan et al., Mathematical Machining Model and Simulation of Limacon Gear Set, College of Mechanical Engineering 2010, 4 pages, Yanshan University, Qinhuangdao, China.

(Continued)

*Primary Examiner* — Theodore Stigell
*Assistant Examiner* — Benjamin Koo
(74) *Attorney, Agent, or Firm* — Fredrikson & Byron, P.A.

(57) ABSTRACT

According to preferred embodiments and methods of the present disclosure, a medical injection system employs a single pump for the injection of multiple fluids, rather than employing a pump for each type of fluid, for example, like the prior art system described above. Embodiments of pumps disclosed herein preferably include a disposable pump cartridge configured to be contained within a hull of a medical injection system, wherein the hull may be formed when a pressure plate member is closed against a base plate; and, when the pressure plate member is opened with respect to the base plate, the disposable pump cartridge may be removed and replaced.

13 Claims, 8 Drawing Sheets

(56) References Cited

U.S. PATENT DOCUMENTS

| | | | |
|---|---|---|---|
| 6,014,791 A * | 1/2000 | Nosenchuck | A47L 5/16 |
| | | | 15/327.1 |
| 6,149,627 A | 11/2000 | Uber, III | |
| 6,168,405 B1 | 1/2001 | Nosenchuck | |
| 6,221,045 B1 | 4/2001 | Duchon et al. | |
| 6,224,572 B1 | 5/2001 | Jacobsen et al. | |
| 8,343,098 B2 * | 1/2013 | Nystrom | A61M 5/007 |
| | | | 604/122 |
| 2004/0101426 A1 | 5/2004 | Wahlberg | |
| 2006/0116631 A1 | 6/2006 | Fukushima | |

FOREIGN PATENT DOCUMENTS

| | | |
|---|---|---|
| EP | 624379 A1 | 7/2001 |
| FR | 2668206 A1 | 4/1992 |
| GB | 860616 A | 2/1961 |
| GB | 2060131 A | 4/1981 |
| JP | 04504498 A | 8/1992 |
| JP | 2001512342 A | 8/2001 |
| JP | 2002528676 A | 9/2002 |
| JP | 5293194 B2 | 9/2013 |
| WO | 9508860 A1 | 3/1995 |
| WO | 2006056828 A1 | 6/2006 |
| WO | 2007141681 A2 | 12/2007 |

OTHER PUBLICATIONS

Ibrahim A. Sultan, A Geometric Design Model for the Circolimaçon Positive Displacement Machine, Journal of Mechanical Design, Jun. 2008, 8 pages, vol. 130.

Ibrahim A. Sultan, Profiling Rotors for Limaçon-to-Limaçon Compression-Expansion Machines, Journal of Mechanical Design, Jul. 2006, vol. 128, pp. 787-793.

Sultan, "The Limacon of Pascal—Mechanical Generation and Utilisation for Fluid Processing," Abstract, 2005.

U.S. Appl. No. 11/877,371, Transmittal and Letter to U.S. Patent and Trademark Office dated Jan. 6, 2009, 5 pages.

* cited by examiner

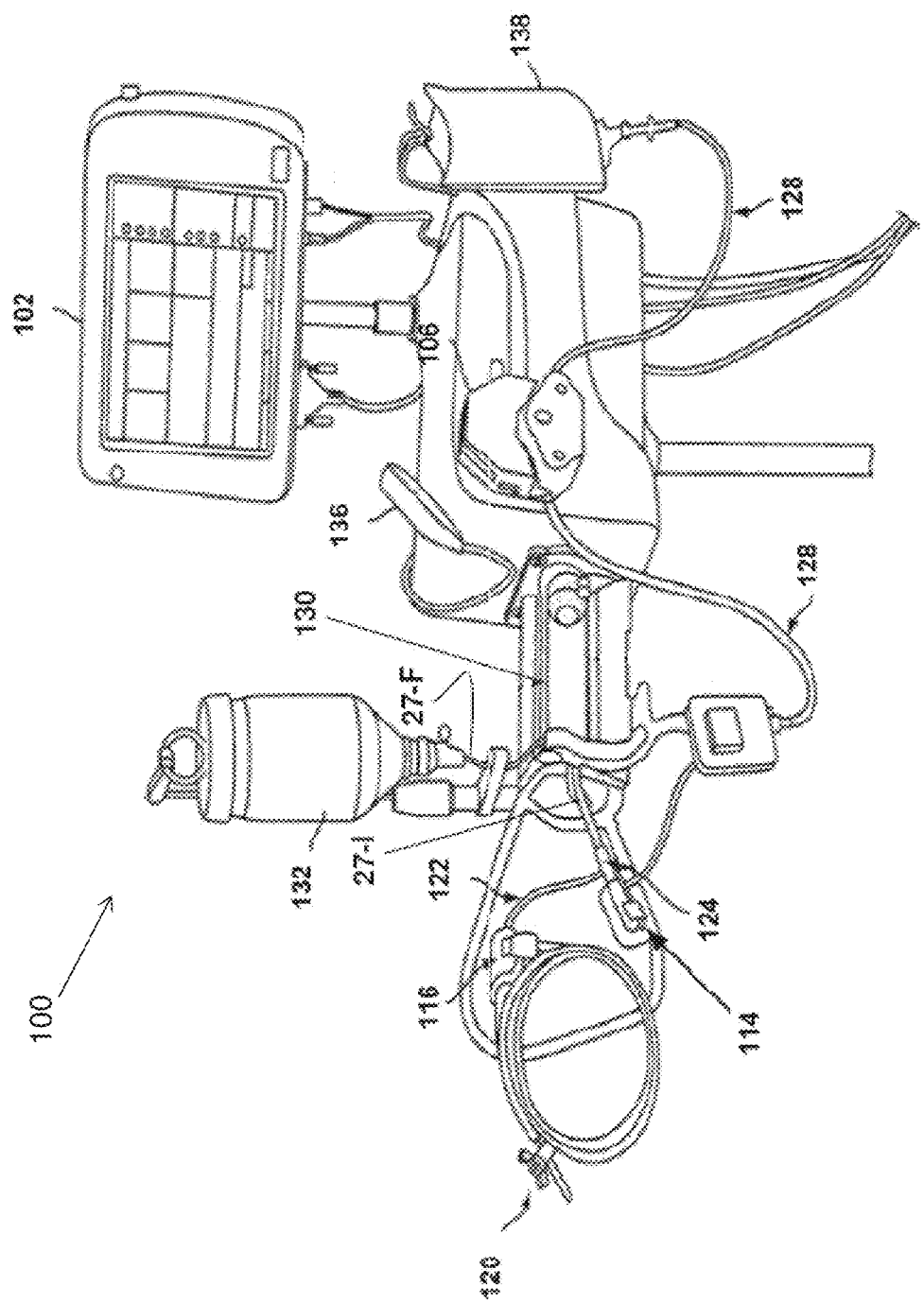
Figure 1 - PRIOR ART

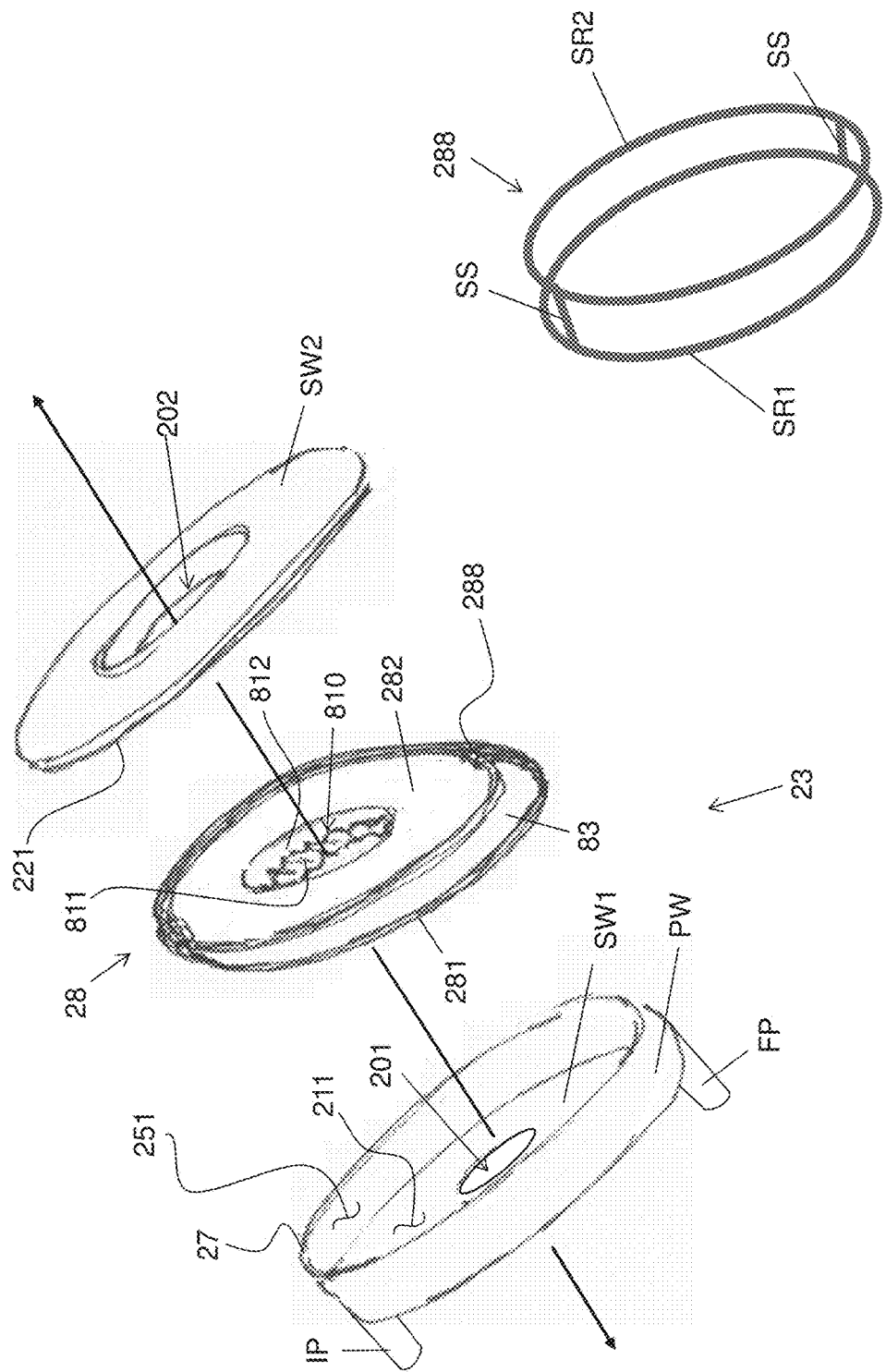

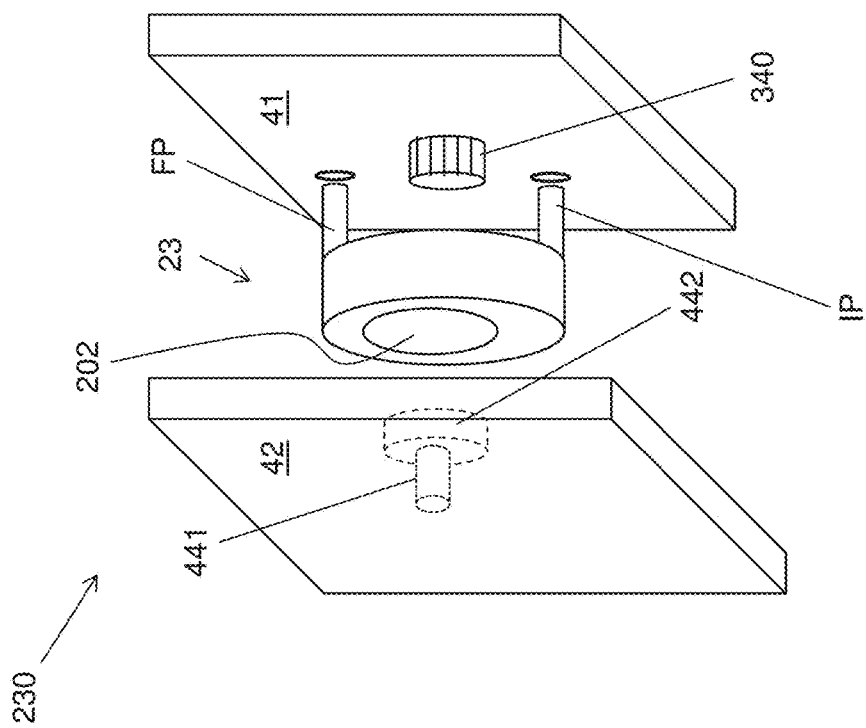

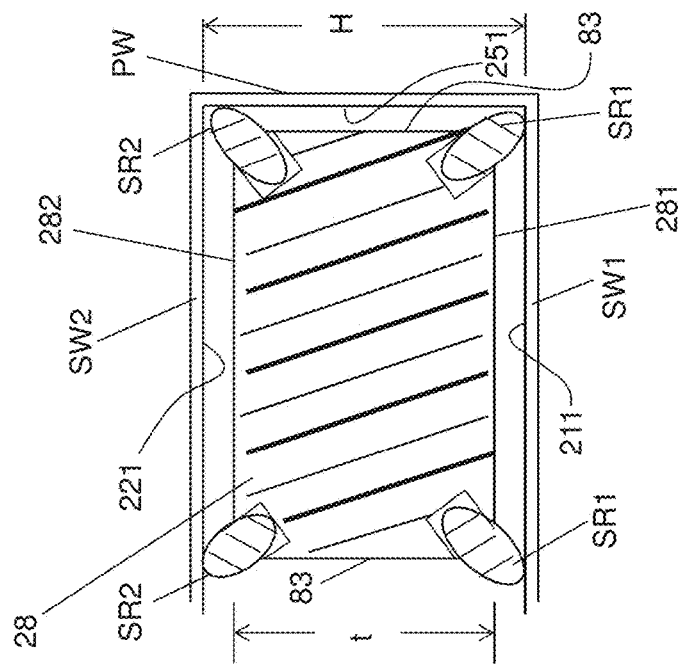
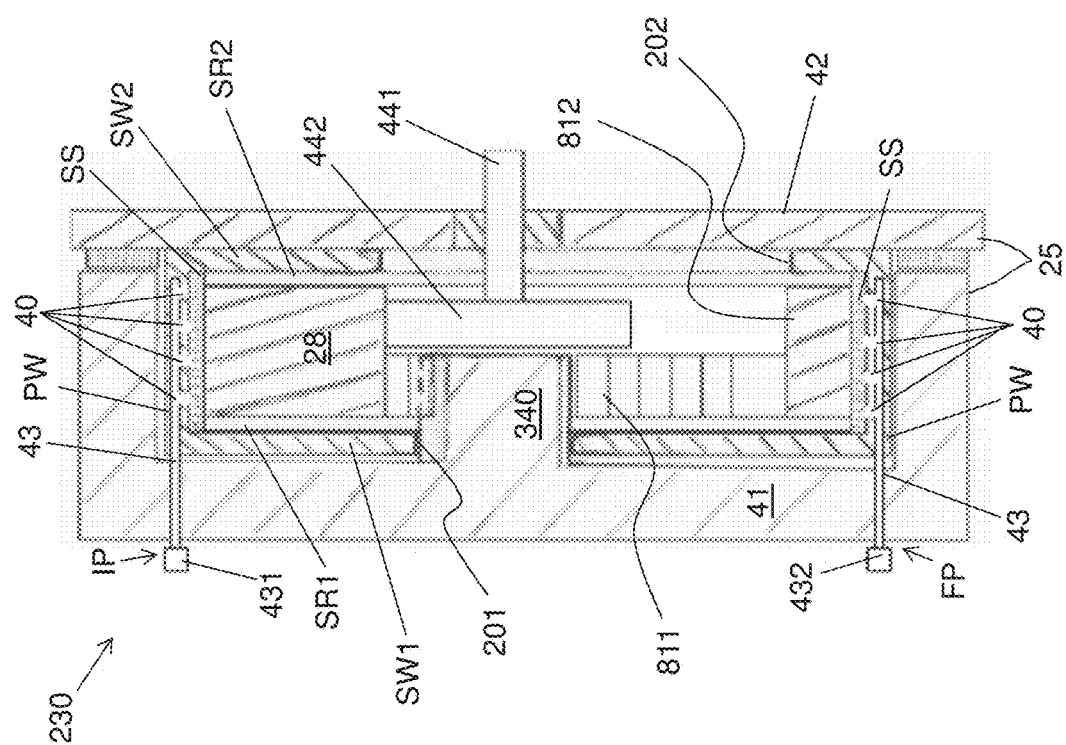
Figure 4B
Figure 4A

MEDICAL INJECTION SYSTEMS AND PUMPS

TECHNICAL FIELD

Embodiments of the present disclosure pertain to medical injection systems and more particularly to the pumps employed therein.

BACKGROUND

FIG. 1 is a perspective view of an exemplary medical injection system 100 (the ACIST CVO system) for delivering a contrast agent into a patient's vascular system for medical imaging. FIG. 1 illustrates a first fluid reservoir 132 for supplying a syringe-type positive displacement pump of a pressurizing unit 130, via a fill tubing line 27-F, and an injection tubing line 27-I coupled to unit 130 for injection of, for example, a radiopaque contrast agent, into a patient's vascular system via an inserted catheter (not shown), for example, coupled to a patient tubing line 122 at a connector 120 thereof. FIG. 1 further illustrates a second fluid reservoir 138 from which a diluent, such as saline, is drawn by a peristaltic pump 106 through yet another tubing line 128 that feeds into tubing line 122. A manifold valve 124 and associated sensor 114 control the flow of fluids into tubing line 122, from pressurizing unit 130 and from tubing line 128.

SUMMARY

According to preferred embodiments and methods of the present disclosure, a medical injection system employs a single pump for the injection of multiple fluids, rather than employing a pump for each type of fluid, for example, like the prior art system described above. Embodiments of pumps disclosed herein preferably include a disposable pump cartridge configured to be contained within a hull of a medical injection system, wherein the hull may be formed when a pressure plate member is closed against a base plate; and, when the pressure plate member is opened with respect to the base plate, the disposable pump cartridge may be removed and replaced.

The disposable pump cartridge preferably includes a shell and a piston, wherein the piston is contained within an inner surface of the shell and includes a bore that is adapted to be operably engaged by a drive member and a fixed gear of the injection system; each of the fixed gear and the drive member are inserted through a corresponding opening formed through the shell, when the cartridge is contained within the hull. The drive member is preferably coupled to a free end of a motor drive shaft, which extends through the base plate, and the fixed gear is preferably mounted to the pressure plate member. According to some preferred embodiments, the disposable pump cartridge is configured to function as a Limaçon-to-Limaçon machine, wherein sliding and rotational motion of the piston is driven by an eccentric drive member of the injection system to create expanding and contracting cavities during pump operation. The piston further includes a pressure seal that extends thereover and is configured to be in sliding and sealing engagement with the inner surface of the shell to seal the expanding and contracting cavities from one another within the shell, and to seal the cavities from the first and second openings of the shell. Fill and injection ports of the shell are preferably located at opposite ends of a long axis of the piston, when the piston is in a position where the contracting cavity is at a maximum volume and the expanding cavity is at a minimum volume.

According to some embodiments, each of the fill and injection ports includes a channel and one or more apertures formed in the inner surface of a perimeter wall of the shell, wherein each channel extends from the corresponding one or more apertures to a corresponding opening in outside the shell. When the disposable cartridge is contained in the hull of the system, the fill and injection ports preferably extend through openings in the pressure plate member, and each has a fitting outside the hull for coupling to a fill and an injection tubing line, respectively, of the system.

BRIEF DESCRIPTION OF THE DRAWINGS

The following drawings are illustrative of particular methods and embodiments of the present disclosure and, therefore, do not limit the scope. The drawings are not to scale (unless so stated) and are intended for use in conjunction with the explanations in the following detailed description. Methods and embodiments will hereinafter be described in conjunction with the appended drawings, wherein like numerals denote like elements, and:

FIG. 1 is a perspective view of an exemplary prior art medical injection system;

FIG. 2B is an exploded perspective view of a disposable pump cartridge that may be employed by the system depicted in FIG. 2A, according to some embodiments;

FIG. 2C is a perspective view of a pressure seal that may be incorporated in the disposable pump cartridge of FIG. 2B, according to some embodiments;

FIG. 2D is an exploded perspective view of a portion of a medical injection system, according to some embodiments;

FIG. 4A is a cross-section view through section line A-A of FIG. 3A, when the disposable pump cartridge is assembled into a hull of the system of FIG. 4A, according to some embodiments;

FIG. 4B is a cross-section view through section line B-B of FIG. 3A, according to some embodiments.

DETAILED DESCRIPTION

The following detailed description is exemplary in nature and is not intended to limit the scope, applicability, or configuration of the disclosure in any way. Rather, the following description provides practical illustrations for implementing exemplary methods and embodiments. Examples of constructions, materials and dimensions are provided for selected elements, and all other elements employ that which is known to those skilled in the art. Those skilled in the art will recognize that many of the examples provided have suitable alternatives that can be utilized.

Figure 2A:
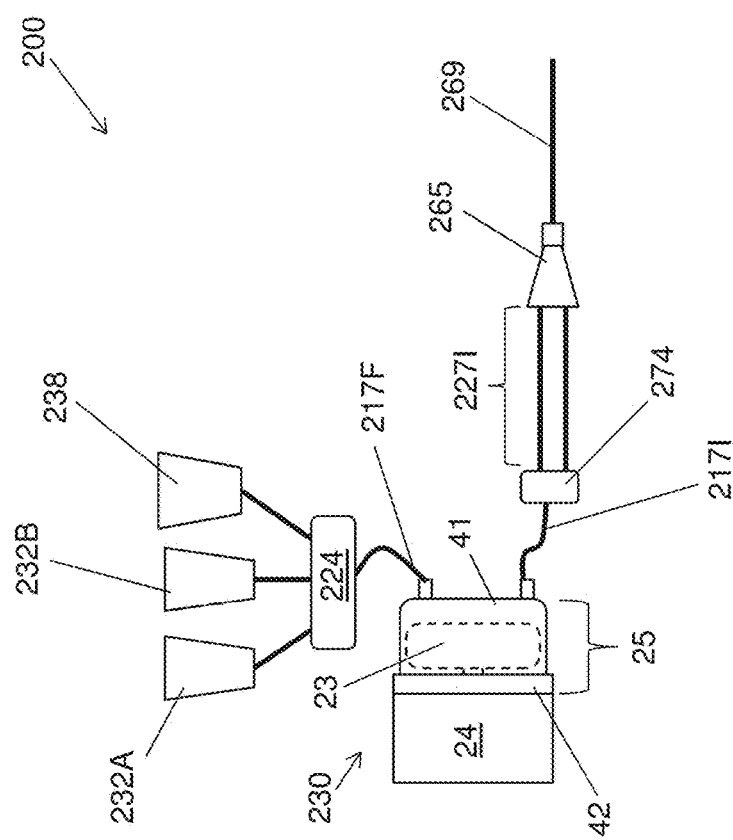
FIG. 2A is a schematic depicting a medical injection system, according to some embodiments of the present disclosure.

FIG. 2A is a schematic depicting a medical injection system 200, according to some embodiments. FIG. 2A illustrates system 200 including a single pump 230, which is coupled between a fill tubing line 217F and an injection tubing line 217I, and which is formed by a hull 25 and a disposable pump cartridge 23 (shown with dashed lines) contained therein. Hull 25 may be formed by a base plate 42 and a pressure plate member 41 that may be opened and closed with respect to base plate 42 to remove and install disposable pump cartridges 23. FIG. 2A further illustrates system 200 including a plurality of fluid reservoirs, for example, two types of contrast agent reservoirs 232A, 232B and a saline reservoir 238, connected to fill tubing line 217F via a manifold assembly 224 (i.e. an inlet stop cock valve) that couples each reservoir 232A, 232B, 238 to pump 230. According to the illustrated embodiment, manifold assembly 224 is controllable to select one of reservoirs 232A, 232B, 238 for filling pump 230 and, once primed, pump 230 is operable simultaneously fill and inject fluid from the selected reservoir.

FIG. 2A shows each of fill tubing line 217F and injection tubing line 217I preferably extending over a limited length, for example, less than approximately 25 mm, and injection tubing line 217I transitioning into a dual lumen line 227I wherein a first lumen is dedicated to contrast agent and a second lumen to saline. Dual lumen line 227I is shown coupled to injection line 217I via a stop-cock valve 274 that can be switched back and forth between the lumens of line 227I, depending on the type of fluid that is being pumped, saline or contrast agent, so as to prevent excessive waste of contrast agent. FIG. 2A further illustrates a y-connector 265 coupling dual lumen line 227I to a patient line 269. According to the illustrated embodiment, y-connector 265 preferably includes a check valve to prevent backflow into dual lumen line 227I. Furthermore, when a pressure transducer is incorporated in line 269 for patient blood pressure monitoring, the check valve helps to improve hemodynamic signal quality by isolating line 269 from line 227I.

FIG. 2B is an exploded perspective view of disposable pump cartridge 23, according to some embodiments. FIG. 2B illustrates cartridge 23 including a shell that has a first sidewall SW1, a second sidewall SW2 and a perimeter wall PW, and a piston 28 configured to be contained within the shell and moved therein to form two dynamically expanding and contracting cavities for drawing in and injecting out, respectively, fluid from any of the aforementioned fluid reservoirs 232A, 232B, 238. With further reference to FIG. 2B, when the shell contains piston 28, a first side 281 of piston 28 extends adjacent to an inner surface 211 of first sidewall SW1, a second side 282 of piston 28 extends adjacent to an inner surface 221 of second sidewall SW2, and an outer perimeter edge 83 of piston 28 extends adjacent to an inner surface 251 of perimeter wall PW. Furthermore an inner perimeter edge of piston 28, which forms a bore 810 through piston 28, includes a first portion 811, located in proximity to a first opening 201 formed through first sidewall SW1 of shell, and a second portion 812 located in proximity to a second opening 202 formed through second sidewall SW2 of shell. According to the illustrated embodiment, first opening 201 allows insertion therethrough of a fixed gear 340 (FIGS. 2D, 4A) to mate with first portion 812 of the inner perimeter edge of piston 28, and second opening 202 allows insertion therethrough of a drive member 442 (FIGS. 2D, 4A) to mate with second portion 812 of the inner perimeter edge, for the operation of pump 230, which is described below.

FIG. 2D is an exploded perspective view of a portion of pump 230, wherein fixed gear 340 may be seen mounted on pressure plate member 41, and drive member 442, which is coupled to a free end of a motor drive shaft 441, is illustrated with dashed lines on a side of base plate 42 that faces second opening 202 of the shell of pump cartridge 23 for the aforementioned engagement with piston 28. It should be noted that suitable bearing supports, known to those skilled in the art of mechanical design, may be employed to support drive shaft 441 as it passes through base plate 41 and to support drive member 442 mounted on the free end of drive shaft 441. With reference to FIGS. 2A and 2D, base plate 42 may be part of a housing 24 that contains the motor from which drive shaft 441 extends, and pressure plate member 41 is coupled to base plate 42, for example, by a hinge and pull action toggle clamp or a pull action cam clamp to form hull 25 that contains pump cartridge 23 and holds pressure during pump operation, and to allow opening and closing of hull 25 for the replacement of disposable pump cartridge 23, for example, after the completion of each imaging procedure. According to preferred embodiments, drive member 442 is a roller bearing mounted eccentric adapted for a toothless engagement with second portion 812 of the inner perimeter edge of piston 28 that facilitates alignment when disposable cartridge 23 is assembled into hull 25.

According to an exemplary embodiment, hull 25 may be formed of stainless steel, while piston 28 and first and second sidewalls SW1, SW2 and perimeter wall PW of the shell are preferably formed, for example by injection molding, from a polycarbonate material, such as APEC® 1745. Each wall of the shell may have a nominal thickness of between approximately 0.070 inch and approximately 0.080 inch, which is preferably uniform along both sidewalls SW1, SW2 and perimeter wall PW, for example, to avoid sink discontinuities from forming during injection molding of the shell. According to the illustrated embodiment, second sidewall SW2 of shell may be formed independently of first sidewall SW1 and perimeter wall PW and then attached about a facing edge 27 of perimeter wall PW, for example by tongue-in-groove engagement and ultrasonic welding or adhesive bonding, wherein the adhesive may be a cyanoacrylate or a UV cure adhesive, or any suitable adhesive known in the art.

With further reference to FIG. 2B, piston 28 includes a pressure seal 288 formed thereover for sliding and sealing engagement with each of the aforementioned inner surfaces of the shell. FIG. 2C is a perspective view of pressure seal 288 separated from piston 28. FIGS. 2B-C illustrate pressure seal 288 including a first seal ring portion SR1 that extends about a perimeter of first side 281 of piston 28, a second seal ring portion SR2 that extends about a perimeter of second side 282 of piston 28, and a pair of seal strip portions SS that extend between first and second seal ring portions SR1, SR2 and along outer perimeter edge 83 of piston 28 opposite one another at either end of a long axis of piston 28. The seal rings and strips of pressure seal 288 are preferably integrally over-molded onto the piston; and, according to an exemplary embodiment, are formed of 917CK silicone rubber (Minnesota Rubber & Plastics of Minneapolis, Minn.) having a hardness of 75+5 on a Shore A scale. According to the illustrated embodiment, pressure seal 288 engages with the inner surfaces of the shell to seal expanding and contracting cavities, which are created by the movement of piston 28 within the shell, from one another and from openings 201, 202.

Figure 3A:
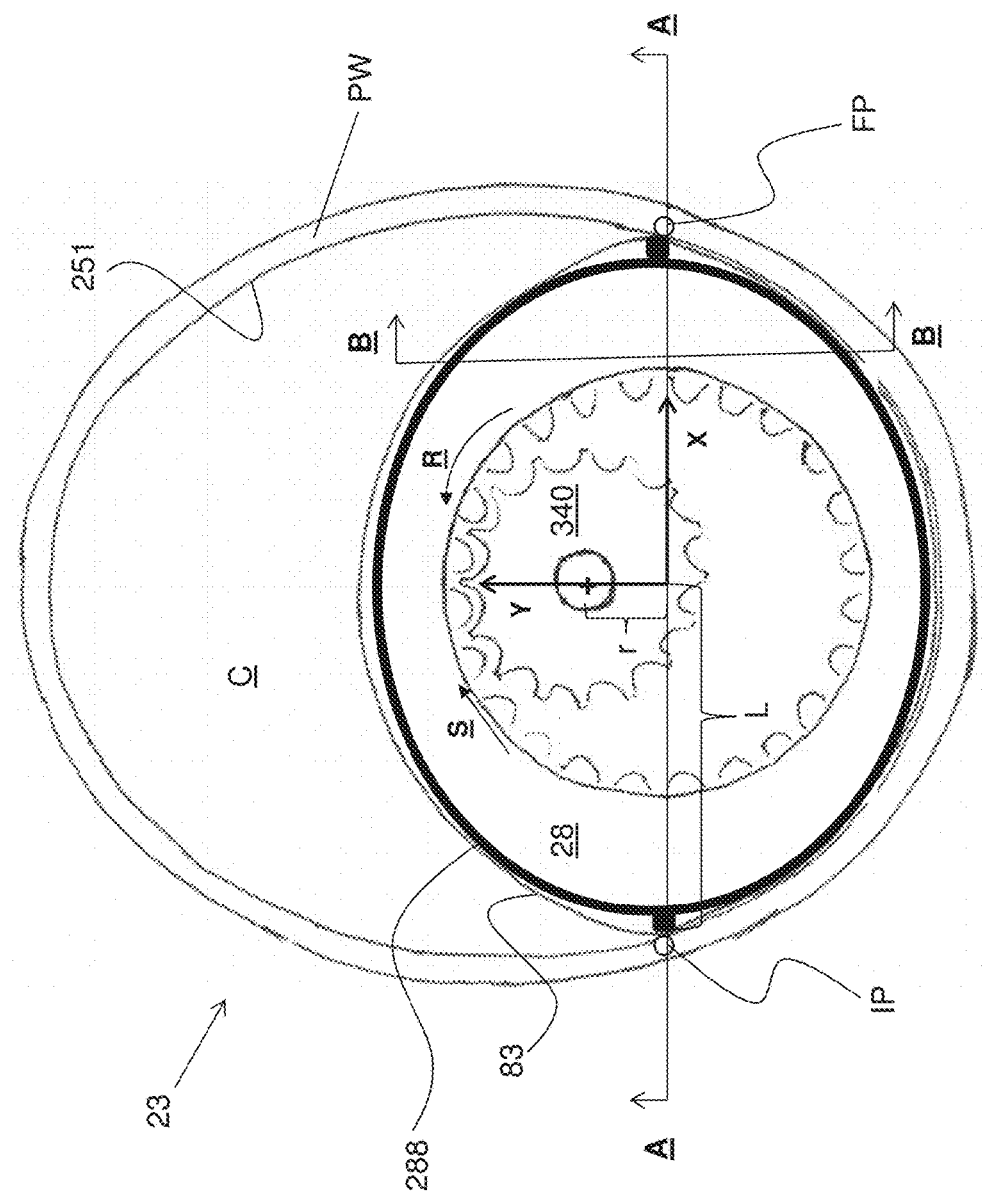
FIG. 3A is a cut-away plan view of an interior of a disposable pump cartridge, according to some embodiments.
Figure 3C:
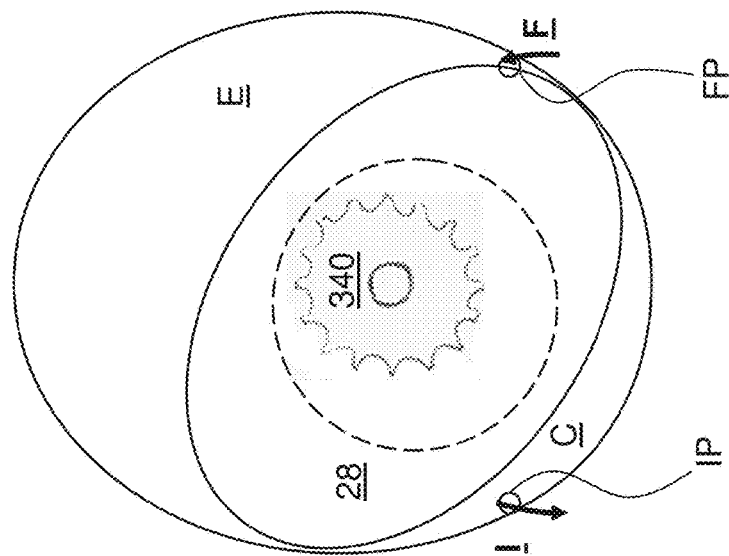
FIGS. 3B-C are schematics depicting exemplary expanding and contracting cavities of the pump cartridge.
Figure 3B:
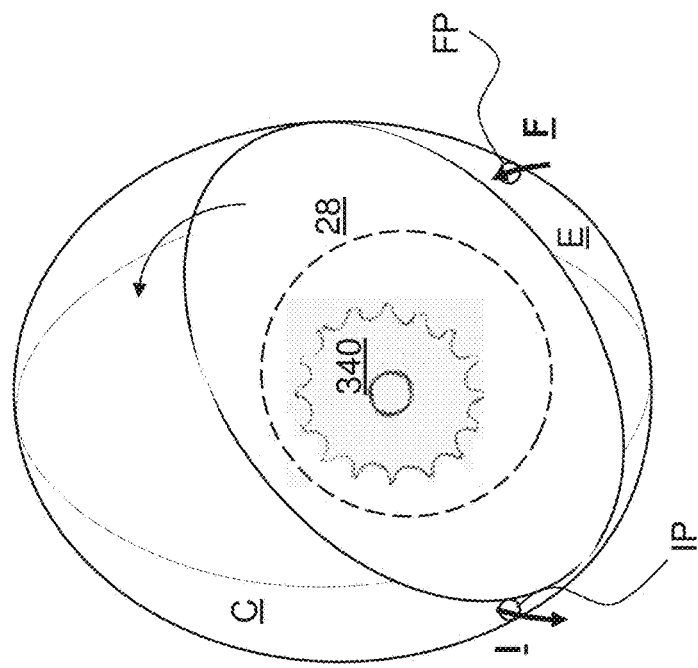

According to some preferred embodiments, disposable pump cartridge 23 is configured to function as a Limaçon-to-Limaçon machine, wherein drive member 442 eccentrically engages with second portion 812 of the inner perimeter edge of piston 28 to cause a sliding and rotational motion thereof, which creates expanding and contracting cavities during pump operation. FIG. 3A is a cut-away plan view of an interior of disposable pump cartridge 23 in which fixed gear 340 is shown engaged with first portion 811 of the inner perimeter edge of the piston 28; and FIGS. 3B-C are schematics showing subsequent positions of piston 28, relative to fixed gear 340 and the shell, as moved by drive member 442—sliding per arrow S and rotating per arrow R (FIG. 3A), to create an expanding cavity E and a contracting cavity C.

With reference to FIG. 3A, a profile of inner surface 251 of perimeter wall PW of the shell conforms to a shape defined by a Limaçon curve in an X-axis, Y-axis coordinate system, wherein the Limaçon is traced by end points of a cord that extends along the X-axis, through the origin of the X-Y coordinate system (over a length equal to twice the length L), and is divided in half by the origin. The Limaçon is represented by the following Cartesian equations:

$$X = r \times \sin(2\theta) + L \times \cos(\theta), \text{ and}$$

$$Y = r - r \times \cos(2\theta) + L \times \sin(\theta);$$

wherein r is a radius of a base circle having a perimeter along which a center point of the cord slides as the end points of the cord rotate about the center point of the cord to trace the Limaçon; r divided by L is less than or equal to 0.25; and θ extends from 0 to 2π. FIG. 3A further illustrates the long axis of piston 28 being approximately the length of the cord (2×L) and having a shape symmetrical across the cord, wherein the curvature of the shape on each side of the cord also conforms to the Limaçon represented by the above equations, but wherein θ extends from π to 2π. Such a Limaçon-to-Limaçon machine is further detailed by Ibrahim A. Sultan in *Profiling Rotors for Limaçon-to-Limaçon Compression-Expansion Machines*, Journal of Mechanical Design, July 2006, Volume 128, pp. 787-793, © 2006 by ASME, which is hereby incorporated by reference. With further reference to FIG. 3A, an injection port IP is located at one end of the long axis of piston 28, and a fill port FP is located at the opposite end of the long axis of piston 28, when piston 28 is at the illustrated dead center position.

With reference to FIG. 3B, piston 28 has been moved counter-clockwise from the dead center position, which is shown in FIG. 3A, to a position at which contracting cavity C is in fluid communication with injection port IP and is beginning to be compressed for injection of fluid, per arrow I, while expanding cavity E is in fluid communication with fill port FP and beginning to be enlarged to draw in fluid, per arrow F. FIG. 3C illustrates a subsequent position of piston 28, having been moved through the position shown with dotted lines in FIG. 3B, at which contracting cavity C is approaching a minimum volume and expanding cavity E is approaching a maximum volume at which it becomes the contracting cavity C of FIG. 3A. The maximum volume of contracting cavity C may be between approximately 2 cubic centimeters and approximately 10 cubic centimeters, wherein a volume closer to 2 cubic centimeters may be preferred for less stress on the shell and piston 28, and in order reduce a waste of fluid when switching from one type to another, for example, from a contrast agent 232A or 232B to saline 238 (FIG. 2A); yet, a volume closer to 10 cubic centimeters will allow the piston to move more slowly thereby reducing wear on pressure seal 288 and decreasing the possibility of fluid cavitation. It should be noted that the volume may be modified by changing the radius r and length L (FIG. 3A) and/or by modifying a height H of inner surface 251 of perimeter wall PW along with a corresponding increase in a thickness t of piston 28 (FIG. 4C).

Turning now to FIGS. 4A-B, which are cross-section views through section lines A-A and B-B, respectively, engagement of the parts of pump 230 may be seen. FIG. 4A illustrates pressure plate member 41 in a closed position with respect to base plate 42 after disposable pump cartridge 23 has been mounted on eccentric drive member 442, by insertion of drive member 442 in through opening 202 of second sidewall SW2 of the shell to engage with second portion 812 of the inner perimeter edge of piston 28. When pressure plate member 41 is closed with respect to base plate 42, fixed gear 340 passes through opening 201 of first sidewall SW1 of the shell to engage with the toothed first portion 811 of the inner perimeter edge of piston 28, wherein the engagement of gear 340 and first portion 811 keep piston 28 'on track' to slide about radius r (FIG. 3A) as drive member 442 rotates piston 28. FIGS. 4A-B further illustrate the engagement of first and second seal ring portions SR1, SR2 of pressure seal 288 extending outward from piston 28 to engage with inner surfaces 211, 221 of first and second shell sidewalls SW1, SW2. According to FIG. 4B, in some embodiments, each of seal rings SR1, SR2 is seated in a groove formed at the intersection of the corresponding one of the first and second sides 281, 282 of piston 28 with outer perimeter edge 83 of piston 28, and a cross-section of each of seal rings SR1, SR2 is preferably oval. The cross-section of seal strips SS may also be oval-shaped, and each may be seated in a corresponding groove extending along outer perimeter edge 83 between first and second sides 281, 282. According to some embodiments each of seal rings SR1, SR2 and seal strips SS extends out from the corresponding groove to contact with corresponding inner surfaces of the shell with a standard compression of approximately 20%, and pressure seal 288 preferably forms the only interface between piston 28 and the inner surfaces of the shell. According to a preferred embodiment, wherein piston 28 is formed from the aforementioned polycarbonate and pressure seal 288 of the aforementioned silicone rubber, pressure seal 288 is directly bonded to piston 28, for example, within the above-described grooves, during the process of over-molding seal 288 onto piston 28.

FIG. 4A further illustrates injection port IP and fill port FP, according to some preferred embodiments, wherein each includes a channel 43 that extends from a corresponding one or more apertures 40, preferably a plurality of apertures, formed in inner surface 251 (FIG. 2B) of perimeter wall PW, such that the above-described fluid communication between each port IP, FP and the corresponding cavity C, E is provided by the corresponding one or more apertures 40. According to the illustrated embodiment, each channel 43 further extends through first sidewall SW1 of the shell and through a corresponding opening formed through pressure plate member 41. With further reference to FIG. 4A, a first fitting 431 is coupled to channel 43 of injection port IP and a second fitting 432 is coupled to channel 43 of fill port FP, wherein first fitting 431 is adapted to couple with injection tubing line 217I and second fitting 432 with fill tubing line 217F outside hull 25 (FIG. 2A). Fittings 431, 432 are preferably different types to assist in the proper connection of injection tubing lines 217F and 217I.

Figure 4C:
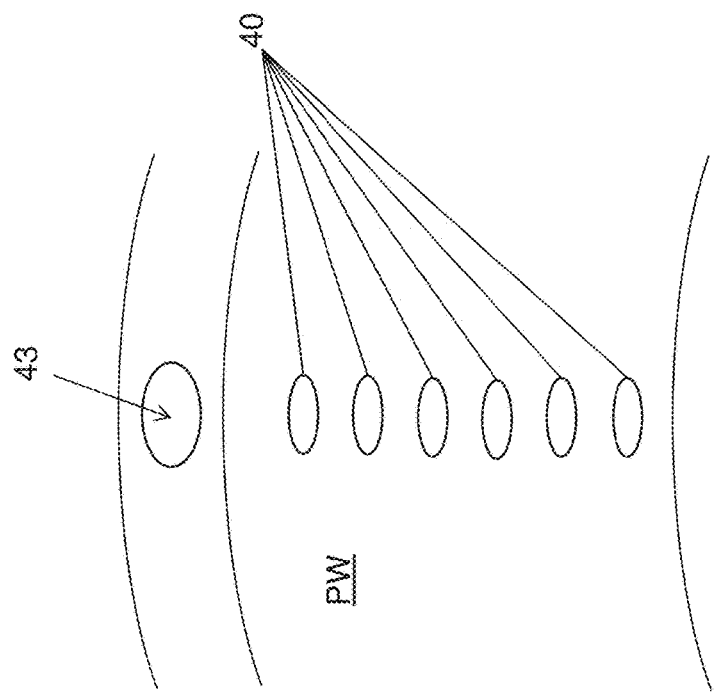
FIG. 4C is an enlarged detail of a portion of a pump cartridge, according to some embodiments.

FIG. 4C is an enlarged detail view of one of channels 43 and the corresponding plurality of apertures 40, according to some embodiments, wherein each aperture has an oval shape with chamfered edges to prevent damage to seal strips SS as each end of the long axis of piston 28 moves past apertures 40. Channel 43 of fill port FP is preferably larger than that of injection port IP, and, according to an exemplary embodiment, a diameter of channel 43 for fill port FP is approximately 8 millimeters and each of the corresponding plurality of apertures 40 is approximately 2 millimeters by 6 millimeters, while a diameter of channel 43 for injection port IP is approximately 3 millimeters and each of the corresponding plurality of apertures is approximately 1 millimeter by 2 millimeters.

In the foregoing detailed description, disclosure subject matter has been described with reference to specific embodiments. However, it may be appreciated that various modifications and changes can be made without departing from the scope of the invention as set forth in the appended claims.

The invention claimed is:

1. A disposable pump cartridge for a medical injection system, the cartridge comprising:
   a shell including a first sidewall, a second sidewall opposite the first sidewall, a perimeter wall extending between the first and second sidewalls, a first opening extending through the first sidewall, a second opening extending through the second sidewall, a fill port, and an injection port, the ports being formed in the perimeter wall, and the shell being configured for the cartridge to be removably assemblable into a hull of the injection system such that the first opening, the second opening, the fill port, and the injection port each align with corresponding hull openings;
   a piston contained within the shell and including a first side, a second side opposite the first side, an outer perimeter edge extending from the first side to the second side, and an inner perimeter edge forming a bore of the piston that extends from the first side to the second side, the inner perimeter edge including a first portion and a second portion, the first portion being configured to engage with a fixed gear of the injection system, the first opening of the shell allowing insertion of the gear through the first opening of the shell and through the corresponding hull opening for the engagement, and the second portion being configured to engage with a drive member of the injection system, the second opening of the shell allowing insertion of the drive member through the second opening of the shell and through the corresponding hull opening for the engagement with the second portion of the piston inner perimeter edge; and
   a pressure seal including a first seal ring, a second seal ring, a first seal strip, and a second seal strip, the first seal ring extending about a perimeter of the first side of the piston, in proximity to the outer perimeter edge, the second seal ring extending about a perimeter of the second side of the piston, in proximity to the outer perimeter edge, the first seal strip extending from the first seal ring to the second seal ring along the outer perimeter edge, and the second seal strip extending from the first seal ring to the second seal ring along the outer perimeter edge and being generally opposite the first seal strip;
   wherein, when the disposable pump cartridge is assembled into the hull of the injection system, the fill port of the shell and a fill tubing line of the injection system are coupled together through the corresponding hull opening, and the injection port of the shell and an injection tubing line of the injection system are coupled together through the corresponding hull opening;
   wherein, when the fixed gear and the drive member of the injection system engage with the piston to move the piston within the shell, an expanding cavity and a contracting cavity are formed within the shell, the expanding cavity being in fluid communication with the fill port, and the contracting cavity being in fluid communication with the injection port; and
   the first seal ring is in sliding and sealing engagement with an inner surface of the first sidewall of the shell to seal the expanding and contracting cavities from one another and from the first opening of the shell, the second seal ring is in sliding and sealing engagement with an inner surface of the second sidewall of the shell to seal the expanding and contracting cavities from one another and from the second opening of the shell, and the first and second seal strips are in sliding and sealing engagement with an inner surface of the perimeter wall of the shell to seal the expanding and contracting cavities from one another.

2. The cartridge of claim 1, wherein a profile of the inner surface of the perimeter wall of the shell conforms to a shape defined by a Limaçon curve.

3. The cartridge of claim 2, wherein the fill and injection ports of the shell are located at opposite ends of a long axis of the piston when the piston is in a position such that the contracting cavity is at a maximum volume and the expanding cavity is at a minimum volume.

4. The cartridge of claim 1, wherein the seal rings and seal strips of the piston are integrally formed as a pressure seal that is over-molded onto the piston.

5. The cartridge of claim 1, wherein each of the fill and injection ports includes a channel and one or more apertures formed in the inner surface of the perimeter wall of the shell, each channel extending along the perimeter wall, between the first and second sidewalls of the shell, and from the corresponding one or more apertures to a corresponding opening outside the shell.

6. The cartridge of claim 5, further comprising a fitting attached to each of the fill and injection ports in proximity to the corresponding opening, each fitting being configured for engagement of a tubing line therewith.

7. The cartridge of claim 5, wherein the channel and the one or more apertures of the fill port are larger than the channel and the one or more apertures of the injection port.

8. The cartridge of claim 2, wherein the seal rings and seal strips of the piston are integrally formed as a pressure seal that is over-molded onto the piston.

9. The cartridge of claim 2, wherein each of the fill and injection ports includes a channel and one or more apertures formed in the inner surface of the perimeter wall of the shell, each channel extending along the perimeter wall, between the first and second sidewalls of the shell, and from the corresponding one or more apertures to a corresponding opening outside the shell.

10. The cartridge of claim 3, wherein the seal rings and seal strips of the piston are integrally formed as a pressure seal that is over-molded onto the piston.

11. The cartridge of claim 3, wherein each of the fill and injection ports includes a channel and one or more apertures formed in the inner surface of the perimeter wall of the shell, each channel extending along the perimeter wall, between the first and second sidewalls of the shell, and from the corresponding one or more apertures to a corresponding opening outside the shell.

12. The cartridge of claim 4, wherein each of the fill and injection ports includes a channel and one or more apertures formed in the inner surface of the perimeter wall of the shell, each channel extending along the perimeter wall, between the first and second sidewalls of the shell, and from the corresponding one or more apertures to a corresponding opening outside the shell.

13. The cartridge of claim 6, wherein the channel and the one or more apertures of the fill port are larger than the channel and the one or more apertures of the injection port.

* * * * *